United States Patent
Lipshutz et al.

(10) Patent No.: US 6,852,895 B2
(45) Date of Patent: Feb. 8, 2005

(54) PRACTICAL, COST-EFFECTIVE SYNTHESIS OF $COQ_{10}$

(75) Inventors: Bruce H. Lipshutz, Goleta, CA (US); Paul Mollard, Saratoga, CA (US)

(73) Assignee: Zymes, Inc., Goleta, CA (US)

( * ) Notice: Subject to any disclaimer, the term of this patent is extended or adjusted under 35 U.S.C. 154(b) by 0 days.

(21) Appl. No.: 10/259,360

(22) Filed: Sep. 27, 2002

(65) Prior Publication Data

US 2003/0073869 A1 Apr. 17, 2003

Related U.S. Application Data

(63) Continuation of application No. 09/639,223, filed on Aug. 15, 2000.

(51) Int. Cl.[7] .......................... C07C 43/02; C07C 43/20
(52) U.S. Cl. ..................... 568/626; 568/630; 568/648; 568/649; 568/650; 568/651; 568/652; 568/654
(58) Field of Search ................................. 568/626, 630, 568/648, 649, 650, 651, 652, 654, 33

(56) References Cited

U.S. PATENT DOCUMENTS

| | | |
|---|---|---|
| 3,313,826 A | 4/1967 | Gale |
| 3,313,831 A | 4/1967 | Gale |
| 4,447,362 A | 5/1984 | Watanabe et al. |

FOREIGN PATENT DOCUMENTS

| | | |
|---|---|---|
| JP | 49080031 | 8/1974 |
| JP | 62286949 | * 12/1987 |
| JP | 04226937 | * 8/1999 |

OTHER PUBLICATIONS

Ohshima et al, Characterization of the Ubiquinone Reduction Siteof Mitochondria Complex I, 1998, Biochemistry, vol. 37 No. 8, pp. 6436–6445.*
Feldman, Cyclization Pathways of a (Z)–Stilbene–Derived Bis(ortho quinone monoketal, 1997, J. of Organic Chemistry, vol. 62 No. 15, pp. 4983–4990.*
Ishii et al, Sythetic studies on naturally occurring coumarins, 1992, Chem. Pharm. Bulletin, vol. 40 No. 10, pp. 2624–19.*
Ishi et al, Convenient Synthesis of courmarins, 1991, Chem. Pharm. Bulletin, vol. 39 No. 11, pp. 3100–3102.*
Seshadri et al, Syntheis of fumigatom, 1959, J. of the Chem. Soc., Abstract, 1660–2.*
Eren, et al., "Total synthesis of linear polyprenoids. 3[1]Syntheses of ubiquinones via palladium–catalyzed oligomerization of monoterpene monomers," J. Am. Chem. Soc., 110:4356–4362 (1988).
Hooz, et al., "Progargylation of Alkyl Halides: Synthesis of (E)–6,10–Dimethyl–5,9–Undecadien–1–YNE and (E)–7, 11–Dimethyl–6,10–Dodecadien–2–YN–1–OL," Org. Syn,, 69:120–129 (1990).
Lipshutz, et al., "A convergent approach to coenzyme Q," J. Am. Chem. Soc.,. 121:11664–11673 (1999).

(List continued on next page.)

Primary Examiner—Alton N. Pryor
(74) Attorney, Agent, or Firm—Morgan, Lewis & Bockius LLP (57) ABSTRACT

The present invention provides a convergent method for the synthesis of ubiquinones and ubiquinone analogues. Also provided are precursors of ubiquinones and their analogues that are useful in the methods of the invention.

14 Claims, 2 Drawing Sheets

OTHER PUBLICATIONS

Lipshutz, et al., "Nickel on charcoal ("Ni/C"): An expedient and inexpensive heretogeneous catalyst for cross–couplings, between aryl chlorides and organometallics. I. fuctionalized organozinc reagents" *J. Am . Chem. Soc.*, 121:5819–5820 (1999).

Lipshutz, et al., "A novel route to coenzyme $Q_n$," *J. Am. Chem. Soc.*, 118:5512–5313 (1996).

Lipshutz, et al., "Biaryls via Suzuki cross–couplings catalyzed by nickel on charcoal," *Tetrahedron*, 56:2139–2144 (2000).

Lipshutz, et al, ."Kumada couplings catalyzed by nickel on charcoal (Ni/C)," *Inorganica Chimica Acta*, 296:164–169 (1999).

Naruta, "Regio– and stereoselective synthesis of coenzymes $Q_n$ (n=2–10), Vitamin K, and related polyprenylquinones," *J. Am. Chem.*, 45:4097–4104 (1980).

Rüttimann, et al., "80. Ein neuer syntheischer Zugang zu Ubichinonen," *Helvetica Chimica Acta*, 73:790–796 (1990).

Sasikala, et at., "Biotechnological potentials of anoxygenic phototropic bacteria. I. Production of single–cell protein, vitamins, ubiquinones, hormones, and enzymes and use in waste treatment," *Adv. Appl. Microbiol.*, 41:173–226 (1995).

Terao, et al., "Synthesis of Ubiquinones. Elongation of the heptaprenyl side–chain in Ubiquinone–7," *J. Chem. Soc., Perkin Trans.*, 1:1101–1110 (1978).

Van Lient, et al., Synthesis and spectroscopic charicterisation of $^{13}$C–labelled ubiquinone–0 and ubiquinone–10, *Recl., Trav. Chim. Pays–Bas*, 113:153–161 (1994).

Yanigisawa, et al., "Highly $S_\pi 2'$–, (E)–, and antiselective alkylation of allylic phosphates. Facile synthesis of coenzyme $Q_{10}$," *Synthesis*, pp. 1130–1136 (1991).

\* cited by examiner

PRACTICAL, COST-EFFECTIVE SYNTHESIS OF COQ$_{10}$

CROSS-REFERENCES TO RELATED APPLICATIONS

This application is a continuation of U.S. application Ser. No. 09/639,223, filed Aug. 15, 2000, the disclosure of which are incorporated herein by reference for all purposes.

BACKGROUND OF THE INVENTION

The ubiquinones, also commonly called coenzyme $Q_n$ (n=1–12), constitute essential cellular components of many life forms. In humans, $CoQ_{10}$ is the predominant member of this class of polyprenoidal natural products and is well-known to function primarily as a redox carrier in the respiratory chain (Lenaz, COENZYME Q. BIOCHEMISTRY, BIOENERGETICS, AND CLINICAL APPLICATIONS OF UIQUINONE, Wiley-Interscience: New York (1985); Trumpower, FUNCTION OF UBIQUINONES IN ENERGY CONSERVING SYSTEMS, Academic Press, New York (1982); Thomson, R. H., NATURALLY OCCURRING QUINONES, 3rd ed., Academic Press, New York (1987); Bliznakov et al., THE MIRACLE NUTRIENT COENZYME $Q_{10}$, Bantom Books, New York (1987)).

Coenzyme Q plays an essential role in the orchestration of electron-transfer processes necessary for respiration. Almost all vertebrates rely on one or more forms of this series of compounds which are found in the mitochondria of every cell (i.e., they are ubiquitous, hence the alternative name "ubiquinones"). Although usually occurring with up to 12 prenoidal units attached to a p-quinone headgroup, $CoQ_{10}$ is the compound used by humans as a redox carrier. Oftentimes unappreciated is the fact that when less than normal levels are present, the body must construct its $CoQ_{10}$ from lower forms obtained through the diet, and that at some point in everyone's life span the efficiency of that machinery begins to drop. (Blizakov et al., supra) The consequences of this in vivo deterioration can be substantial; levels of $CoQ_{10}$ have been correlated with increased sensitivity to infection (i.e., a weakening of the immune system), strength of heart muscle, and metabolic rates tied to energy levels and vigor. In some countries (e.g., Japan), $CoQ_{10}$ is treated as a "drug", prescribed especially for those having suffered from heart disease, and is among the leading pharmaceuticals sold. In the United States, however, it is considered a dietary supplement, sold typically in health food stores or through mail order houses at reasonable prices. It is indeed fortunate that quantities of $CoQ_{10}$ are available via well-established fermentation and extraction processes (e.g., Sasikala et al., Adv. Appl. Microbiol., 41:173 (1995); U.S. Pat. Nos. 4,447,362; 3,313,831; and 3,313,826) an apparently more cost-efficient route relative to total synthesis. However, for producing lower forms of CoQ, such processes are either far less efficient or are unknown. Thus, the costs of these materials for research purposes are astonishingly high, e.g., $CoQ_6$ is ~$22,000/g, and $CoQ_9$ is over $40,000/g. (Sigma-Aldrich Catalog, Sigma-Aldrich: St. Louis, pp. 306–307 (1998)).

Several approaches to synthesizing the ubiquinones have been developed over the past 3–4 decades, attesting to the importance of these compounds. Recent contributions have invoked such varied approaches as Lewis acid-induced prenoidal stannane additions to quinones, (Naruta, J. Org. Chem., 45:4097 (1980)) reiterative Pd(0)-catalyzed couplings of doubly activated prenoidal chains with allylic carbonates bearing the required aromatic nucleus in protected form (Eren et al., J. Am. Chem. Soc., 110:4356 (1988) and references therein), and a Diels—Alder, retro Diels—Alder route to arrive at the quinone oxidation state directly (Van Lient et., Rec. Trav. Chim. Pays-Bays 113:153 (1994); and Rüttiman et al., Helv. Chim. Acta, 73:790 (1990)). Nonetheless, all are lengthy, linear rather than convergent, and/or inefficient. Moreover, problems in controlling double bond stereochemistry using, e.g., a copper(I)-catalyzed allylic Grignard-allylic halide coupling can lead to complicated mixtures of geometrical isomers that are difficult to separate given the hydrocarbon nature of the side chains (Yanagisawa, et al., Synthesis, 1130 (1991)).

For the reasons set forth above, a convergent method for the synthesis of the ubiquinones and their analogues which originates with a simple benzenoid precursor and procedes with retention of the double bond stereochemistry would represent a significant advance in the synthesis of ubiquinones and their analogues. The present invention provides such a method and ubiquinone precursors of use in the method.

SUMMARY OF THE INVENTION

The present invention provides an efficient and inexpensive method for preparing ubiquinones and structural analogues of these essential molecules. Also provided are new compounds that are structurally simple and provide a convenient, efficient and inexpensive entry into the method of the invention.

Thus, in a first aspect, the present invention provides a compound according to Formula I:

(I)

In Formula I, $R^1$, $R^2$ and $R^3$ are independently selected $C_1$–$C_6$ alkyl groups, preferably methyl groups. $R^4$ represents H or a protecting group. $R^5$ is selected from branched, unsaturated alkyl, —C(O)H, and —CH$_2$Y, in which Y is $OR^6$, $SR^6$, $NR^6R^7$, or a leaving group. $R^6$ and $R^7$ are independently selected from H and branched, unsaturated alkyl.

In a second aspect, the present invention provides a method for preparing a compound according to Formula IV:

(IV)

In Formula IV, each of $R^1$, $R^2$ and $R^3$ is an independently selected $C_1$–$C_6$ alkyl group and the subscript n represents an integer from 0 to 13.

The method of the invention comprises, contacting a compound according to Formula V:

(V)

with a compound according to Formula VI:

(VI)

In Formula V, $R^1$, $R^2$, $R^3$ are as discussed above. Y is a leaving group and $R^4$ is a protecting group. In Formula VI, L is an organometallic ligand; M is a metal; p is an integer from 1 to 5; and n is an integer from 0 to 13. Each of the organometallic ligands, L, can be the same or different.

The compounds according to Formulae V and VI are contacted in the presence of a catalyst that is effective at catalyzing coupling between a benzylic carbon atom, such as that in Formula V and an organometallic species according to Formula VI. The coupling of the compounds of Formulae V and VI, forms a compound according to Formula VII:

(VII)

The protecting group $R^4$ is preferably removed from the compound according to Formula VII to produce a compound according to Formula VII to produce a compound according to Formula VIII:

(VIII)

The phenol is oxidized to the quinone of Formula IV, by contacting the compound according to Formula VIII with an oxidant.

Other objects and advantages of the invention will be apparent to those of skill in the art from the detailed description that follows.

DETAILED DESCRIPTION OF THE INVENTION AND THE PREFERRED EMBODIMENTS

Definitions

The term "alkyl," by itself or as part of another substituent, means, unless otherwise stated, a straight or branched chain, or cyclic hydrocarbon radical, or combination thereof, which may be fully saturated, mono- or poly-unsaturated and can include di- and multi-valent radicals, having the number of carbon atoms designated (i.e. $C_1-C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)ethyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below as "heteroalkyl," "cycloalkyl" and "alkylene." The term "alkylene" by itself or as part of another substituent means a divalent radical derived from an alkane, as exemplified by —$CH_2CH_2CH_2CH_2$—. Typically, an alkyl group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" refer to those groups having an alkyl group attached to the remainder of the molecule through an oxygen, nitrogen or sulfur atom, respectively. Similarly, the term "dialkylamino" is used in a conventional sense to refer to —NR'R" wherein the R groups can be the same or different alkyl groups.

The term "acyl" or "alkanoyl" by itself or in combination with another term, means, unless otherwise stated, a stable straight or branched chain, or cyclic hydrocarbon radical, or combinations thereof, consisting of the stated number of carbon atoms and an acyl radical on at least one terminus of the alkane radical.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S($O)_2$—$CH_3$, —CH=CH—O—$CH_3$, —Si($CH_3)_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3)_3$. Also included in the term "heteroalkyl" are those radicals described in more detail below as "heteroalkylene" and "heterocycloalkyl." The term "heteroalkylene" by itself or as part of another substituent means a divalent radical derived from heteroalkyl, as exemplified by —CH$_2$—CH$_2$—S—CH$_2$CH$_2$— and —CH$_2$—S—CH$_2$—CH$_2$—NH—CH$_2$—. For heteroalkylene groups, heteroatoms can also occupy either or both of the chain termini. Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "fluoroalkyl," are meant to include monofluoroalkyl and polyfluoroalkyl.

The term "aryl," employed alone or in combination with other terms (e.g., aryloxy, arylthioxy, arylalkyl) means, unless otherwise stated, an aromatic substituent which can be a single ring or multiple rings (up to three rings), which are fused together or linked covalently. "Heteroaryl" are those aryl groups having at least one heteroatom ring member. Typically, the rings each contain from zero to four heteroatoms selected from N, O, and S, wherein the nitrogen and sulfur atoms are optionally oxidized, and the nitrogen atom(s) are optionally quaternized. The "heteroaryl" groups can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl ring systems are selected from the group of acceptable substituents described below. The term "arylalkyl" is meant to include those radicals in which an aryl group is attached to an alkyl group (e.g., benzyl, phenethyl, pyridylmethyl and the like) or a heteroalkyl group (e.g., phenoxymethyl, 2-pyridyloxymethyl, 3-(1-naphthyloxy)propyl, and the like).

Each of the above terms (e.g., "alkyl," "heteroalkyl" and "aryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from, for example: —OR', =O, =NR', =N—OR', —NR'R", —SR', -halogen, —SiR'R"R'", —OC(O)R', —C(O)R', —CO$_2$R', CONR'R", —OC(O)NR'R", —NR"C(O)R', —NR'—C(O)NR"R'", —NR"C(O)$_2$R', —NH—C(NH$_2$)=NH, —NR'C(NH$_2$) =NH, —NH—C(NH$_2$)=NR', —S(O)R', S(O)$_2$R', —S(O)$_2$NR'R", —CN and —NO$_2$ in a number ranging from zero to (2N+1), where N is the total number of carbon atoms in such radical. R', R" and R'" each independently refer to hydrogen, unsubstituted (C$_1$–C$_8$)alkyl and heteroalkyl, unsubstituted aryl, aryl substituted with 1–3 halogens, unsubstituted alkyl, alkoxy or thioalkoxy groups, or aryl-(C$_1$–C$_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similarly, substituents for the aryl groups are varied and are selected from: -halogen, —OR', —OC(O)R', —NR'R", —SR', —R', —CN, —NO$_2$, —CO$_2$R', —CONR'R", —C(O) R', —OC(O)NR'R", —NR"C(O)R', —NR"C(O)$_2$R', —NR', —C(O)NR"R'", —NH—C(NH$_2$)=NH, —NR'C(NH$_2$) =NH, —NH—C(NH$_2$)=NR', —S(O)R', —S(O)$_2$R', —S(O)$_2$NR'R", —N$_3$, —CH(Ph)$_2$, perfluoro(C$_1$–C$_4$)alkoxy, and perfluoro(C$_1$–C$_4$)alkyl, in a number ranging from zero to the total number of open valences on the aromatic ring system; and where R', R" and R'" are independently selected from hydrogen, (C$_1$–C$_8$)alkyl and heteroalkyl, unsubstituted aryl, (unsubstituted aryl)-(C$_1$–C$_4$)alkyl, (unsubstituted aryl) oxy-(C$_1$–C$_4$)alkyl and perfluoro(C$_1$–C$_4$)alkyl.

Two of the substituents on adjacent atoms of the aryl ring may optionally be replaced with a substituent of the formula —T—C(O)—(CH$_2$)$_q$—U—, wherein T and U are independently —NH—, —O—, —CH$_2$— or a single bond, and the subscript q is an integer of from 0 to 2. Alternatively, two of the substituents on adjacent atoms of the aryl ring may optionally be replaced with a substituent of the formula —A—(CH$_2$)$_r$—B—, wherein A and B are independently —CH$_2$—, —O—, —NH—, —S—, —S(O)—, —S(O)$_2$—, —S(O)$_2$NR'—or a single bond, and r is an integer of from 1 to 3. One of the single bonds of the new ring so formed may optionally be replaced with a double bond. Alternatively, two of the substituents on adjacent atoms of the aryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$–C$_6$)alkyl.

As used herein, the term "heteroatom" is meant to include, for example, oxygen (O), nitrogen (N), sulfur (S) and silicon (Si).

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I)or carbon-14 ($^{14}$C). All isotopic variations of the compounds of the present invention, whether radioactive or not, are intended to be encompassed within the scope of the present invention.

As used herein, the term "leaving group" refers to a portion of a substrate that is cleaved from the substrate in a reaction.

"Protecting group," as used herein refers to a portion of a substrate that is substantially stable under a particular reac- tion condition, but which is cleaved from the substrate under a different reaction condition. A protecting group can also be selected such that it participates in the direct oxidation of the aromatic ring component of the compounds of the invention. For examples of useful protecting groups, see, for example, Greene et al., PROTECTIVE GROUPS IN ORANIC SYNTHESIS, John Wiley & Sons, New York, 1991.

Introduction

The present invention provides an efficient and cost-effective route to the ubiquinones and their analogues. The present method is quite general and can be used to afford precursors to $CoQ_n$ and analogues as well as systems found in vitamins $K_1$ and $K_2$ and their analogues. The invention also provides compounds that are useful in the method of the invention.

The Compounds

In a first aspect, the invention provides a compound according to Formula I:

(I)

In Formula I, $R^1$, $R^2$ and $R^3$ are independently selected $C_1$–$C_6$ alkyl groups, preferably methyl groups. $R^4$ represents H or a protecting group. When $R^4$ is a protecting group, it is preferably a group in which $R^4$ and the phenolic oxygen to which $R^4$ is attached form a sulfonate ester. $R^5$ is selected from branched, unsaturated alkyl, —C(O)H, and —CH$_2$Y, in which Y is $OR^6$, $SR^6$, $NR^6R^7$, or a leaving group. $R^6$ and $R^7$ are independently selected from H and branched, unsaturated alkyl. When Y is a leaving group, it is preferably a halogen, and more preferably a chloro group.

In a further preferred embodiment $R^5$ has a structure according to Formula II:

(II)

In Formula II, n is a member selected from the integers from 0 to 13, and preferably from 4 to 10.

In a preferred embodiment, the invention provides a compound having a structure according to Formula III:

(III)

In the compounds according to Formula III, $R^5$ is preferably as discussed above.

Synthesis

The compounds of the invention are synthesized by an appropriate combination of generally well-known synthetic methods. Techniques useful in synthesizing the compounds of the invention are both readily apparent and accessible to those of skill in the relevant art. The discussion below is offered to illustrate certain of the diverse methods available for use in assembling the compounds of the invention, it is not intended to define the scope of reactions or reaction sequences that are useful in preparing the compounds of the present invention.

A representative synthetic scheme setting forth the preparation of selected compounds of the invention is displayed below in Scheme 1.

a. DIBAL—H/THF;
b. LiCl/DMF; MsCl; Et$_3$N

In Scheme 1,3,4-dimethoxy-6-methyl-2-toluenesulfonyloxybenzaldehyde i is converted to the corresponding alcohol ii by the action of a reducing agent, such as DIBAL-H. The alcohol is converted to the corresponding chloride iii by treatment with lithium chloride, methanesulfonyl chloride and triethylamine.

A representative scheme leading to a selected compound of the invention in which $R^5$ is a branched, unsaturated alkyl is set forth in Scheme 2.

In Scheme 2, the benzylic halide iii is contacted with a vinylalane in the presence of a Ni(0) catalyst. The vinyl moiety and the carbon at the benzylic position couple, affording compound iv.

Figure 1:
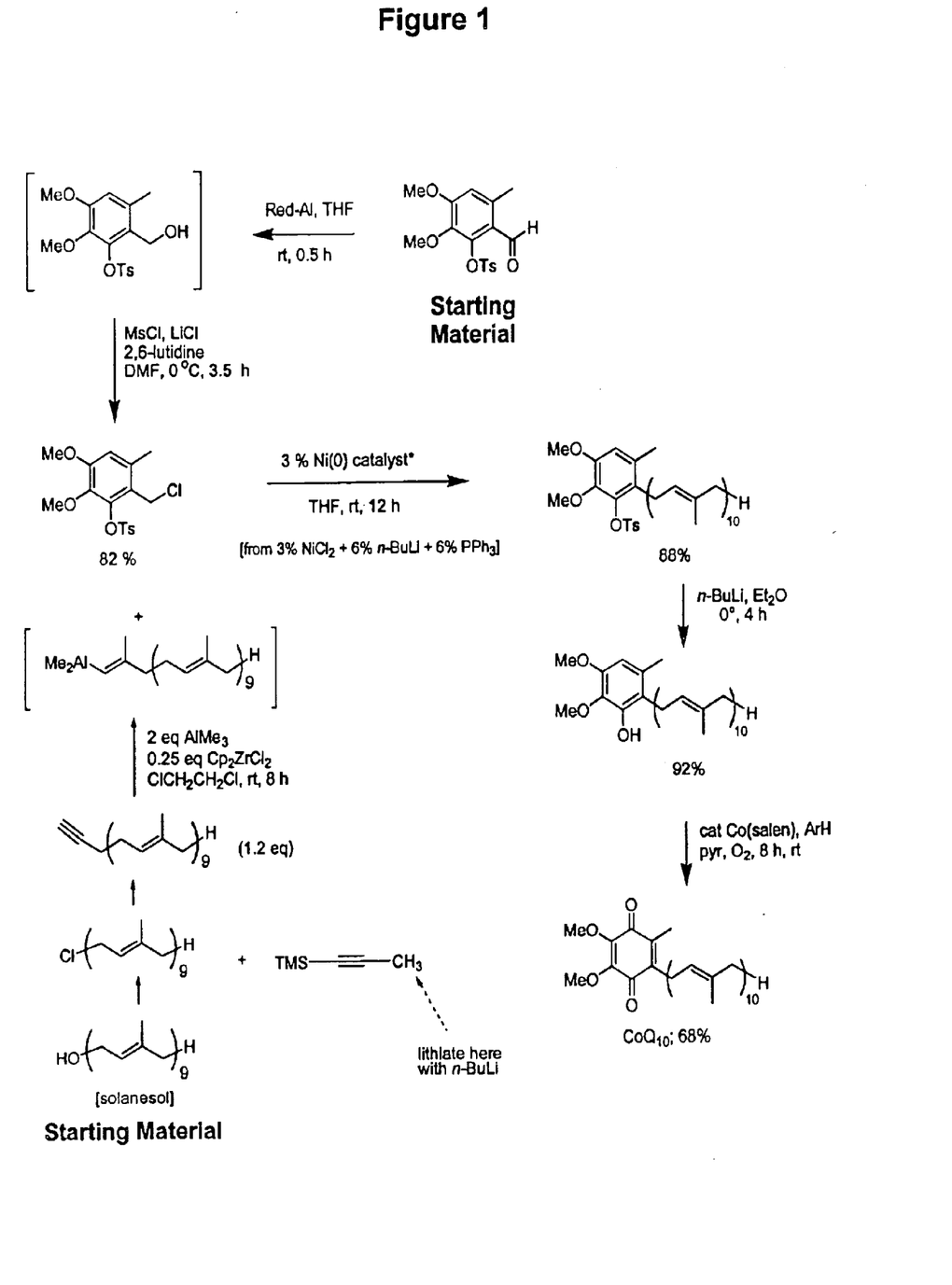
FIG. 1 is a representative synthetic scheme for the process of the invention in which a trimethylsilyl-protected three-carbon fragment is utilized to form an exemplary alkene moiety of a ubiquinone.

Compounds in which $R^5$ is CH$_2$Y and Y is $OR^6$, $SR^6$ or $NR^6R^7$ are prepared by art-recognized means or modifications thereof. In an exemplary scheme, Y is $OR^6$, and $R^6$ is a branched, unsaturated alkyl group derived from the alcohol solanesol (FIG. 1). The alcohol fragment is coupled to the benzylic position using chloride iii, under conditions appropriate for preparing a benzylic ether (e.g., Williamson synthesis using the sodium salt of the alcohol; White et al., *J. Am. Chem. Soc.* 83: 3268 (1961)). In another exemplary scheme, Y is $SR^6$ and $R^6$ is again derived from solanesol. The intermediate thiol, $HSR^6$ is prepared from the corresponding alcohol by, for example, treating the alcohol with Lawesson's reagent (Nishio, *J. Chem. Soc. Chem. Commun.* 205 (1989)), or a fluoropyridinium salt and sodium N,N-dimethylthiocarbamate (Hojo et al., *Chem. Lett.* pp. 133, 437 (1977)). The resulting thiol is converted to the corresponding thiolate ion, as in the Williamson synthesis, and reacted with the benzylic chloride iii. In yet a further exemplary scheme, in which Y is $NR^6R^7$, solanesol is converted to the corresponding amine by, for example, the action of hydrazonic acid, diidopropyl azodicarboxylate and excess $PPh_3$ in THF (Fabiano et al, *Synthesis*, 190 (1987)). The resulting amine is coupled to the carbon at the benzylic position through the chloride iii.

In each of the reaction pathways described above, purification of the end-products and the intermediates, where necessary, is accomplished by substantially any means known in the art including, for example, precipitation, crystallization and chromatography (e.g., TLC, column, flash, HPLC) or a combination thereof.

The above-recited synthetic schemes are intended to be exemplary of the synthesis of one compound of the invention. Those of skill in the art will recognize that many other synthetic strategies leading to compounds within the scope of the present invention are available. For example, by a slight modification of the starting material above, a compound having ethoxy, rather than methoxy groups is produced. Moreover, both the leaving and protecting groups shown in Scheme 1 can be replaced with other useful groups.

The reaction pathway set forth in Scheme 1 can be altered by using a leaving group other than a chloro at the benzylic position. Useful leaving groups include, but are not limited to, halides, sulfonic esters, oxonium ions, alkyl perchlorates, ammonioalkanesulfonate esters, alkylfluorosulfonates and fluorinated compounds (e.g., triflates, nonaflates, tresylates) and the like. The choice of these and other leaving groups appropriate for a particular set of reaction conditions is within the abilities of those of skill in the art (see, for example, March J, ADVANCED ORGANIC CHEMISTRY, 2nd Edition, John Wiley and Sons, 1992; Sandler S R, Karo W, ORGANIC FUNCTIONAL GROUP PREPARATIONS, 2nd Edition, Academic Press, Inc., 1983; and Wade L G, Compendium of ORGANIC SYNTHETIC METHODS, John Wiley and Sons, 1980).

In a presently preferred embodiment, the leaving group, Y, is a halogen, more preferably, a chloro group.

Moreover, the p-toluenesulfonyl group used to protect the phenol oxygen atom in Scheme 1 can be replaced with a number of other art-recognized protecting groups. Useful phenol protecting groups include, but are not limited to, ethers formed between the phenol oxygen atom and substituted or unsubstituted alkyl groups (e.g., methyl, methoxymethyl, benzyloxymethyl, methoxyethoxymethyl, 2-(trimethylsilyl)ethoxymethyl, methylthiomethyl, phenylthiomethyl, 2,2-dichloro-1,1-difluoroethyl, tetrahydropyranyl, phenacyl, p-bromophenacyl, cyclopropylmethyl, allyl, isopropyl, cyclohexyl, t-butyl, benzyl, 2,6-dimethylbenzyl, 4-methoxybenzyl, o-nitrobenzyl, 2,6-dichlorobenzyl, 4-(dimethylaminocarbonyl)benzyl, 9-anthrymethyl, 4-picolyl, heptafluoro-p-tolyl, tetrafluoro-4-pyridyl); silyl ethers (e.g., trimethylsilyl, t-butyldimethylsilyl); esters (e.g., acetate, levulinate, pivaloate, benzoate, 9-fluorenecarboxylate); carbonates (e.g., methyl, 2,2,2-trichloroethyl, vinyl, benzyl); phosphinates (e.g., dimethylphosphinyl, dimethylthiophosphinyl); sulfonates (e.g., methanesulfonate, toluenesulfonate, 2-formylbenzenesulfonate), and the like (see, e.g., Greene et al., PROTECTIVE GROUPS IN ORANIC SYNTHESIS, John Wiley & Sons, New York, 1991).

The Methods

In one aspect, the method of the present invention is based on a retrosynthetic disconnection that relies on the well-known maintenance of olefin geometry in group 10 coupling reactions (Hegedus, TRANSITION METALS IN THE SYNTHESIS OF COMPLEX ORANIC MOLECULES, University Science Books, Mill Valley, Calif. 1994). The discussion that follows focuses on a reaction, in which the coupling partners are a vinyl organometallic and a species with a benzylic position having a leaving group thereon. The focus of the discussion is for clarity of illustration, and other methods and coupling partners appropriate for use in those methods will be apparent to those of skill in the art and are within the scope of the present invention.

Thus, the present invention provides a method for preparing a compound according to Formula IV:

(IV)

In Formula IV, each of $R^1$, $R^2$ and $R^3$ is independently selected from $C_1$–$C_6$ alkyl groups and the subscript n is an integer from 0 to 13.

Figure 2:
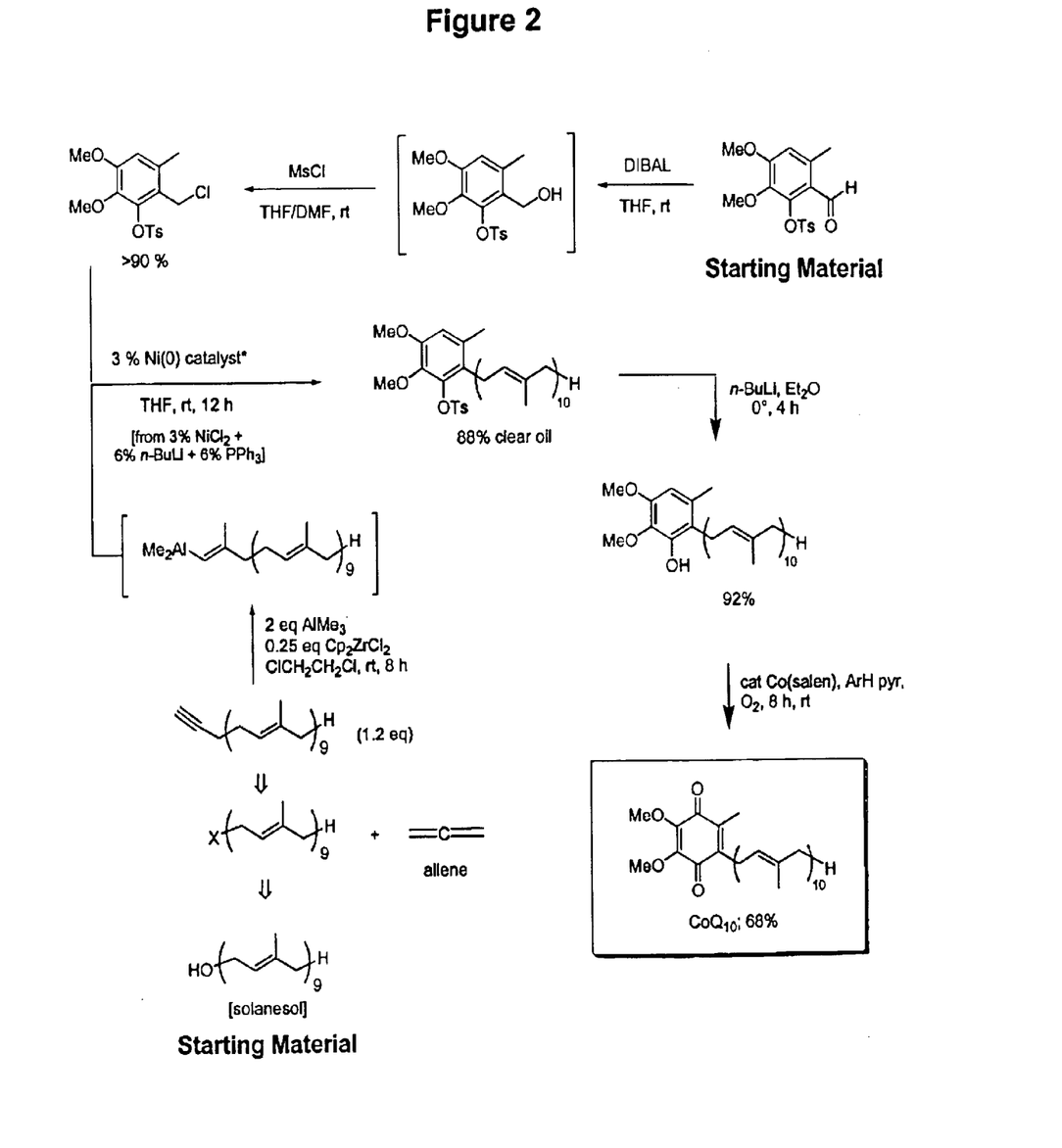
FIG. 2 is a representative synthetic scheme for the process of the invention in which allene is utilized as a three-carbon fragment to form an exemplary alkene moiety of a ubiquinone.

Referring to FIG. 1 and FIG. 2, the method of the invention comprises, contacting a compound according to Formula V:

(V)

in which Y is a leaving group and $R^4$ is a protecting group, with a compound according to Formula VI:

(VI)

In Formula VI, L is an organometallic ligand; M is a metal ion; p is an integer from 1 to 5; and n is an integer from 0 to 13. Each of the organometallic ligands, L, can be the same or different.

The two compounds are contacted in the presence of a catalyst that is effective at catalyzing coupling between a benzylic carbon atom, such as that in Formula V and an organometallic species according to Formula VI. The coupling of the compounds of Formulae V and VI, forms a compound according to Formula VII:

The protecting group $R^4$ is preferably removed from the compound according to Formula VII to produce a compound according to Formula VIII:

The resulting phenol is oxidized to the quinone of Formula IV, by contacting the compound according to Formula VIII with an oxidant.

As discussed above, the aromatic precursor according to Formula V, can include substantially any useful phenol protecting group as $R^4$. Preferred $R^4$ groups are removed by a reaction that is a member selected from the group consisting of hydrolysis, hydrogenolysis, reduction, oxidation, nucleophilic attack, electrophilic attack and combinations thereof. In a presently preferred embodiment, $R^4$ is —S(O)$_2R^9$. $R^9$ is preferably substituted or unsubstituted alkyl or substituted or unsubstituted aryl, and more preferably p-tolyl. In a still further preferred embodiment, the p-toluenesulfonyl group is removed by contacting the compound with a mixture comprising n-butyllithium, thereby producing the compound according to Formula VIII.

The alkoxy and alkyl substituents of the phenyl ring system, $R^1$, $R^2$, and $R^3$ are substituted or unsubstituted, branched- or straight-chain, cyclic or non-cyclic alkyl groups that are fully saturated or that include one or more degrees of unsaturation. Moreover, each of $R^1$, $R^2$, and $R^3$ is selected independently and these groups are either the same or different. In a presently preferred embodiment, the method of the invention utilizes a substrate in which each of $R^1$, $R^2$, and $R^3$ is a methyl group.

The ubiquinones and their analogues include an alkene unit, which in the higher homologues (i.e., n≧2) repeats in a precise and predictable manner. The method of the invention is appropriate for synthesizing a ubiquinone or ubiquinone analogue having an alkene component that repeats as many times as is desired. In a presently preferred embodiment n is an integer from 2 to 11, more preferably from 3 to 10.

The metals, M, of use in the method of the invention include those metals that can carbometalate the alkyne component of the reaction pathway to produce a species according to Formula VI. Presently preferred metals include transition metals and aluminum, of which aluminum is presently preferred. The metal can be formally neutral or it can be charged (e.g. an aluminate). The transition metal chemistry can be catalytic or stoichiometric. For example, the alkyne can be metalated by catalytic carbocupration using Cu(I) to form and adduct that is subsequently transmetalated to the corresponding zinc reagent.

The coordination number of M is satisfied by the bonding or coordination to the metal ion of the requisite number of organometallic ligands, such as Lewis base donors (e.g., halogen donors, oxygen donors, mercaptide ligands, nitrogen donors, phosphorous donors, and heteroaryl groups); hydrides; carbon ligands bound principally by σ-bonds (e.g., alkyls, aryls, vinyls, acyl and related ligands); carbon ligands bound by σ- and π-bonds (e.g., carbonyl complexes, thiocarbonyl, selenocarbonyl, tellurocarbonyl, carbenes, carbynes, σ-bonded aetylides, cyanide complexes, and isocyanide complexes); ligands bound through more than one atom (e.g., olefin complexes, ketone complexes, acetylene complexes, arene complexes, cyclopentadienyl complexes, π-allyl complexes); unsaturated nitrogen ligands (e.g., macrocyclic imines, dinitrogen complexes, nitric oxide complexes, diazonium complexes); and dioxygen complexes. Other useful combinations of metal ions and ligands will be apparent to those of skill in the art. See, for example, Collman J P et al. PRINCIPLES AND APPLICATIONS OF ORGANOTRANSITION METAL CHEMISTRY, University Science Books, 1987.

In another preferred embodiment, the catalysis of the coupling utilizes a species that comprises a transition metal. Exemplary transition metal species of use as catalysts include, but are not limited to, Cu(I), Pd(0), Co(0) and Ni(0). Recent reports have demonstrated that couplings, using the appropriate reaction partners and based on metal catalysis, are quite general and can be used to directly afford known precursors (Naruta, *J. Org. Chem.*, 45:4097 (1980); Eren, et al., *J. Am. Chem. Soc.*, 110:4356 (1988) and references therein; Van Lient et al., *Rec. Trav. Chim. Pays-Bays* 113:153 (1994); Rüttiman et al., *Helv. Chim. Acta*, 73:790 (1990); Terao et al., *J. Chem. Soc.*, Perkin Trans. 1:1101 (1978), Lipshutz et al., *J. Am. Chem. Soc.* 121: 11664–11673 (1999); Lipshutz et al., *J. Am. Chem. Soc.* 118: 5512–5313 (1999)). In a preferred embodiment, the metal is Ni(0).

The catalyst can be formed by any of a variety of methods recognized in the art. In a preferred embodiment, in which the transition metal is Ni(0), the catalyst is formed by a method comprising, contacting NiCl$_2$(PPh$_3$)$_2$, or a similar Ni species, with about two equivalents of a reducing agent (e.g., n-butyllithium), thereby reducing said NiCl$_2$(PPh$_3$)$_2$ to Ni(0). Alternatively, other readily available forms of Ni(0) can be employed (e.g., Ni(COD)$_2$).

The method of the invention is practiced with any useful amount of catalyst. In a preferred embodiment, the catalyst is present in an amount from about 0.1 mole % to about 10 mole %, more preferably from about 2 mole % to about 5 mole %.

The catalyst can be a homogeneous or heterogeneous catalyst (Cornils B, Herrmann W A, APPLIED HOMOGENEOUS CATALYSIS WITH ORGANOMETALLIC COMPOUNDS: A COMPREHENSIVE HANDBOOK IN TWO VOLUMES, John Wiley and Sons, 1996; Clark J H, CATALYSIS OF ORGANICE REACTIONS BY SUPPORTED INORGANIC REAGENTS, VCH Publishers, 1994; Stiles A B, CATALYST SUPPORTS AND SUPPORTED CATALYSTS: THEORETICAL AND APPLIED CONCEPTS, Butterworth-Heinemann, 1987). In one preferred embodiment, the catalyst is supported on a solid material (e.g., charcoal, silica, etc.). In another preferred embodiment, the catalyst is a supported nickel catalyst (see, e.g., Lipshutz et al., *Tetrahedron* 56:2139–2144 (2000); Lipshutz and Blomgren, *J. Am. Chem. Soc.* 121: 5819–5820 (1999); and Lipshutz et al., *Inorganica Chimica Acta* 296: 164–169 (1999).

The aromatic portion of the species synthesized by the method of the invention is generally oxidized to the corresponding quinone. The phenol can be oxidized directly to the quinone or, alternatively, it can first be converted to the corresponding hydroquinone and oxidized to the quinone. An array of reagents and reaction conditions are known that oxidize phenols to quinones, see, for example, Trost B M et al. COMPREHENSIVE ORGANIC SYNTHESIS: OXIDATION, PERGAMON Press, 1992.

In a preferred embodiment, the oxidant comprises a transition metal chelate. The chelate is preferably present in the reaction mixture in an amount from about 0.1 mol % to about 10 mol %. In another preferred embodiment, the transition metal chelate is used in conjunction with an organic base, such as an amine. Presently preferred amines are the trialkyl amines, such as triethylamine. In another preferred embodiment, the transition metal chelate is Co(salen). The chelate can be a heterogeneous or homogeneous oxidant. In a preferred embodiment, the chelate is a supported reagent.

The alkene component of the reaction pathway of the invention can be prepared by any of a number of methods known in the art for assembling such compounds. In an exemplary art-recognized method, an allylsulfone moiety is coupled to an allyl chloride to form the desired polyene (see, e.g., Lipshutz et al., *J Am. Chem. Soc.* 121: 11664–11673 (1999)). The sulfone moiety serves as a control element for the synthesis of the polyprenoidal derivatives. The use of the sulfone derivatives allows for the facile scale-up of the reactions assembling the polyprenoidal component of the ubiquinones and their analogues.

In a preferred embodiment, the compound according to Formula VI is produced by a method comprising contacting a compound according to Formula IX:

(IX)

with a compound according to Formula X:

(X)

in the presence of a base.

In Formula IX, $Y^1$ is a leaving group, as discussed above. In a preferred embodiment, the leaving group is a halogen, more preferably a chloro group.

In Formula X, $R^8$ is substituted or unsubstituted alkyl, substituted or unsubstituted aryl, substituted or unsubstituted heteroalkyl. Each of the $R^8$ groups is independently selected and they are the same or different.

The anion of a compound according to Formula X, is contacted with a compound according to Formula IX, thereby forming a compound according to Formula XI:

(XI)

The anion is formed in situ or, alternatively, it is formed prior to combining the constituents of the reaction. The anion is formed with an appropriate base, which is preferably an organolithium base. The compound according to Formula XI is subsequently desilylated to produce a compound according to Formula XII:

(XII)

The compound of Formula XII is then carbometalated to produce a compound according to Formula VI:

(VI)

in which, as discussed above, L is an organometallic ligand; M is a metal ion; and p is a member selected from the integers from 1 to 5. Each of the p organometallic ligands, L, is independently selected.

Referring to FIG. 2, in a further method, a compound of Formula VI is formed by coupling a compound according to Formula IX to an allene to add the necessary three carbon fragment. The coupling between allene and a compound of Formula IX is preferably facilitated by the presence of an organolithium base (see, for example, Hooz et al., *Org. Syn.* 69: 120 (1990)).

In yet another preferred embodiment, the compound according to Formula V is produced by a method comprising contacting a compound according to Formula XIII:

(XIII)

with a reducing agent, thereby forming a compound according to Formula XIV:

(XIV)

The compound according to Formula XIV, which in this state or as the corresponding alkoxide is contacted with a reagent that converts the —OH group into a leaving group, preferably a halogen, thereby forming a compound according to Formula V. Alternatively, the intermediate formed after contacting compound XIII with a reducing agent is converted directly to the corresponding halide by contacting the intermediate with a protic halide source, such as a hydrohalic acid (e.g., hydrochloric, hydrobromic, etc.).

In those embodiments in which Y is a halogen, it is preferably a chloro group. A presently preferred chlorinating reagent mixture comprises, MsCl; LiCl; and an amine. A preferred amine is a trialkylamine, such as triethylamine.

A wide array of art-recognized reducing agents can be used to effect the transformation of the aldehyde of Formula XIII to the alcohol of Formula XIV. See, for example, Trost B M, et al., COMPREHENSIVE ORGANIC SYNTHESIS: REDUCTION, PERGAMON Press, 1992. In a presently preferred embodiment, the reducing agent is a reagent that is a source of hydrogen which is a member selected from the group consisting of metal hydrides, and catalytic hydrogenation. In another preferred embodiment, the reduction is an electrochemical reduction.

In another aspect, the present invention provides a method of preparing the quinones of the invention by direct alkylation of a quinone having a reactive benzylic position. In this aspect, a compound according to Formula XV:

(XV)

is coupled to an alkyl moiety using an organometallic reagent, preferably in which the alkyl component is a branched, unsaturated moiety. Each of the preferred embodiments of the aspects of the invention discussed above are generally applicable to the present aspect as well. The synthesis of quinones functionalized with a halomethyl group can be accomplished using methods such as that described by Lipshutz et al., *J. Am. Chem. Soc.* 121: 11664–11673 (1999)), the disclosure of which is incorporated herein by reference.

In Formula XV, $R^{10}$, $R^{11}$ and $R^{12}$ are each independently selected from substituted or unsubstituted alkyl, substituted or unsubstituted heteroalkyl, substituted or unsubstituted aryl, substituted or unsubstituted heterocyclyl and substituted or unsubstituted heteroaryl. $R^{10}$ and $R^{11}$ are optionally joined together to form a ring system having from 5 to 7 members. In a presently preferred embodiment, $R^{10}$ and $R^{11}$ are alkoxy and $R^{12}$ is alkyl. In a further preferred embodiment, $R^{10}$ and $R^{11}$ are methoxy and $R^{12}$ is methyl. $R^{13}$ is a leaving group, preferably a chloro group.

Also within the scope of the present invention is a method of preparing a hydroquinone derivative as set forth in Scheme 3.

Scheme 3

In Scheme III, $R^1$, $R^2$, $R^3$ and n are as described previously. $R^{40}$ and $R^{41}$ are independently selected from H, (=O) and —$OR^{42}$ and —$OR^{43}$. $R^{42}$ and $R^{43}$ are independently selected from H and protecting groups. $R^{44}$ and $R^{45}$ are independently selected from H, substituted or unsubstituted alkyl, substituted or unsubstituted heteroalkyl and acyl groups.

In an exemplary reaction pathway, a quinone of Formula IV is prepared by a method of the invention and is subsequently reduced to the corresponding hydroquinone by, for example, $LiAlH_4$, $SnCl_2$—HCl, sodium hydrosulfite, or another appropriate reducing agent. Methods of preparing hydroquinones in which $R^{42}$ and $R^{43}$ are protecting groups (e.g., Si-based protecting groups) and methods of selectively removing these protecting groups are known in the art (see, for example, Greene et al., PROTECTIVE GROUPS IN ORANIC SYNTHESIS, John Wiley & Sons, New York, 1991). In yet a further exemplary reaction pathway, the hydroquinone is prepared and one or more of the phenolic oxygen atoms is subsequently derivatized. Examples of useful derivatives include, but are not limited to, O-alkyl, and O-acyl derivatives. In a still further exemplary route, the synthetic pathway originates with a protected hydroquinone that is coupled with a vinylalane. Also provided are compounds prepared by the route exemplified by Scheme 3.

The materials, methods and devices of the present invention are further illustrated by the examples which follow. These examples are offered to illustrate, but not to limit the claimed invention.

EXAMPLES

The following Examples provide representative synthetic procedures that are useful to practice the method of the invention. Example 1 sets forth a representative synthesis of a prenoidal species useful in practicing the present invention. Example 2 describes an alternate route for removing the TMS group from a TMS-protected alkyne, such as that prepared in Example 1. Example 3 details a preparation of a representative precursor for the aromatic portion of a compound prepared by a method of the invention. Example 4 sets forth a Ni mediated coupling of an alkyne and a representative aromatic moiety to provide a cross-coupled product. Example 5 describes a method useful for deprotecting the aromatic portion of a species synthesized by a method of the invention. Example 6 sets forth an oxidation of a phenol prepared by a method of the invention to the corresponding quinone.

Example 1

1.1 Preparation of Reagents $PCl_3$ was refluxed for 3 h at 76° C. while slowly purging with dry argon to expel HCl, distilled at atmospheric pressure and stored in a sealed container under argon until needed. DMF, 2-propanol and benzene were used as supplied from Fisher chemicals. Solanesol, purified by column chromatography on $SiO_2$ with 10% diethyl ether/petroleum ether, was dried azeotropically with toluene or benzene immediately prior to use. THF was distilled from Na/benzophenone ketyl prior to use. n-BuLi was obtained as a 2.5 M solution in hexanes from Aldrich and standardized by titration immediately prior to use. Ethanol was 200 proof, dehydrated, U.S.P. Punctilious grade. All other reagents were used as supplied by their respective vendors. Products were confirmed by $^1H$ NMR, IR, LREIMS and HR-EI or HR-CI Mass Spectrometry.

1.2 Chlorination of Solanesol

DMF (5.0 mL) was cooled to 0° C. and $PCl_3$ (370 μL, 3.30 mmol) was added slowly such that the reaction warmed but was never hot to the touch. Stirring was suspended, the ice bath removed and the reaction let stand until a solid had formed (1.25 h). The reaction was recooled to 0° C., stirring resumed and solanesol (2.97 g, 4.7 mmol) in 5 mL benzene was added with benzene (2×1 mL) to complete the transfer.

The ice bath was removed after addition of solanesol and the reaction was monitored by TLC. After 0.5 h the reaction was carefully poured onto petroleum ether (30 mL) and saturated NaHCO$_3$ solution (30 mL) and ice. The layers were separated and the aqueous layer extracted with petroleum ether (3×10 mL), the combined organics washed once with saturated brine solution (20 mL) and dried over anhydrous MgSO$_4$. The product was concentrated to a clear brown oil via rotary evaporation and dried azeotropically with toluene (2×5 mL) prior to use in the next step.

1.3 Alkylation of Lithiated TMS-propyne

THF (20 mL) at −78° C. was charged with 1.26 mL n-BuLi (2.48 M in hexanes, 3.13 mmol) and after 5 min, 490 μL TMS-propyne (355 mg, 3.17 mmol) were added. After 1.5 h at −78° C., the reaction was warmed to −20° C. for 0.75 h then recooled to −50° C. Crude chloride (2.10 g, 3.17 mmol) dissolved in 10 mL THF was cooled to −50° C. and added slowly via cold cannula. The reaction was warmed to rt over 3.5 h and quenched by addition of 1 mL saturated NH$_4$Cl solution, and the brown mixture concentrated via rotary evaporation to a brown oil. The residue was dissolved in 20 mL water and 20 mL petroleum ether and the layers separated. The aqueous phase was extracted 3×10 mL hexanes and the combined organics washed with 20 mL brine, dried over anhydrous Na$_2$SO$_4$ and concentrated in vacuo. Flash chromatography 5% CH$_2$Cl$_2$/petroleum ether gave the product as a clear, colorless oil which solidified upon standing 1.91 g (83%).

1.4 Deprotection of the TMS-protected Alkyne

The crude material from the alkylation was dried azeotropically with benzene (3×5 mL), after which ethanol (20 mL) and 2-propanol (7 mL) were added. The mixture was warmed to 35° C. to dissolve the crude alkyne. K$_2$CO$_3$ (850 mg, 6.2 mmol) was added. After stirring overnight, the mixture was poured onto water (50 mL) and diethyl ether (20 mL). The layers were separated and the aqueous layer was extracted with diethyl ether (3×10 mL). The combined organics were washed once with saturated brine solution (10 mL), dried with anhydrous MgSO$_4$ and concentrated in vacuo. Column chromatography with 1% diethyl ether/petroleum ether yielded 1.39 g of a pale yellow oil (59% based on n-BuLi).

Example 2

2.1 Reagents

Ethanol was obtained from Rossville, Gold Shield U.S.P. grade 95% and stored in a sealed metal container. Sodium metal was stored under toluene and cut fresh just prior to addition to ethanol. TMS-Alkyne was purified by column chromatography and was a clear oil of >95% purity by $^1$H NMR.

2.1a Preparation of Sodium Ethoxide

Ethanol (10 mL, 95%) was placed in an open container with a slow stream of argon passing over it, sodium (53 mg, 2.31 mmol) was carefully added and allowed to dissolve. The theoretical concentration of NaOEt was 0.154 M.

2.2 Removal of TMS Group

TMS-Alkyne (256 mg, 0.353 mmol) in a 10 mL round bottom flask with a stir bar was charged with 2.8 mL of the sodium ethoxide solution (0.425 mmol, 0.15 M in NaOEt) and a reflux condenser attached. The biphasic solution was heated to 60–65° C. in a oil bath for 4 h. The reaction was poured onto 10 mL of deionized H$_2$O and 10 mL of petroleum ether, the layers were separated, the aqueous layer extracted three times with 10 mL petroleum ether and the combined organics washed once with 10 mL saturated NaCl, dried over anhydrous Na$_2$SO$_4$ and concentrated in vacuo. Chromatography of the residue with 10% CH$_2$Cl$_2$/petroleum ether gave 228 mg of a clear oil (99%). Purity was confirmed by $^1$H NMR as >95% pure.

Example 3

3.1 Synthesis

3,4-Dimethoxy-6-methyl-2-toluenesulfonyloxybenzaldehyde (2.68 g, 7.65 mmol, R$_f$=0.28) in dry THF (8.0 mL) was stirred at 0° C. under argon in a 50 mL round bottom flask fitted with a double septa capped Claisen head. DIBAL-H (8.3 mL, Aldrich 21,498-1, 1.0 M in THF) was added dropwise via syringe over 5 min. The reaction was stirred for 1.5 h at which time TLC showed all but a trace of tosyloxy aldehyde had been consumed, giving a new spot corresponding to the tosyloxy benzyl alcohol (R$_f$=0.18). While maintaining the temperature at 0° C., DMF (5.0 mL, Aldrich 22,705-6) was added via syringe followed by dry LiCl (1.0 g, 22.9 mmol) in one portion through the Claisen head. Methanesulfonyl chloride (1.63 g, 1.10 mL, 14.2 mmol) was added dropwise via syringe followed by triethylamine (1.0 g, 1.35 mL, 9.7 mmol). After 60 min, the cooling bath was removed and the reaction was stirred at room temperature for 10 h after which time TLC showed all but a trace of the tosyloxy benzyl alcohol had been consumed giving a new spot corresponding to the tosyloxy benzyl chloride (R$_f$=0.49).

The light yellow heterogeneous crude reaction mixture was poured into a 500 mL separatory funnel containing citric acid (4.5 g, 21.4 mmol) dissolved in water (180 mL), and the remaining residue was transferred to the funnel with ethyl acetate (3×25 mL). The combined organic portions were shaken well against the yellow aqueous solution and then separated. The yellow aqueous layer was further extracted with ethyl acetate (3×100 mL). The organic portions were combined and stripped in vacuo leaving a pale yellow colored solid which was taken up in ethyl acetate (300 mL) in a 500 mL shaking funnel and washed with a saturated ammonium chloride solution (200 mL). The layers were separated and the organic portion was washed with brine (200 mL). The layers were separated and the organic portion was shaken vigorously for 5 min with anhydrous sodium sulfate (10 g). The funnel was drained through a cotton plug into an Erlenmeyer flask containing anhydrous sodium sulfate (50 g) and the solution allowed to stand for 5 h. The dried solution was filtered through a glass frit (150 mL; 40–60 course grade) which had been layered with Celite (Aldrich 22,179-1, 3 cm), followed by a layer of activated charcoal (Aldrich 27,810-6, 1 cm), and finally a third layer of Celite (2 cm). The filter cake was rinsed with ethyl acetate (4×50 mL) and the combined organic portions stripped in vacuo leaving 2-chloromethyl-4,5-dimethoxy-3-tosyloxytoluene as a white solid (2.61 g, 7.0 mmol, yield 92%; 96% pure by GCMS integration).

Example 4

This reaction consists of three distinct portions; carboalumination of alkyne 1, preparation of the Ni(0) complex, and combination of the carboaluminated alkyne 2 with chloromethylated tosylate 3 and the Ni(0) catalyst to give cross-coupled product 4.

4.1 Carboalumination of Alkyne 1

Cp$_2$ZrCl$_2$ (74 mg, 0.25 mmol) and AlMe$_3$ (0.5 mL, 2.0 M in hexanes, 1.0 mmol) were combined and about 90% of the solvent was removed in vacuo. The gray-white residue was then dissolved in ClCH$_2$CH$_2$Cl (DCE) (0.5 mL) giving a pale yellow solution. Alkyne (325 mg, 0.5 mmol) in DCE (0.25 mL) was added via cannula (exothermic) followed by washings with DCE (2×0.125 mL) to complete the transfer. After 11 h at room temperature, the solvent was completely removed from the heterogeneous yellow mixture in vacuo. The residue was triturated hexanes (3×3 mL) and the hexanes removed in vacuo to remove all traces of DCE. To the heterogeneous yellow mixture was then added hexanes (2 mL) and the resulting supernatant was cannulated away from the residual Zr salts. The salts were washed twice with hexanes (2×1 mL) which were combined with the original washing. The combined clear yellow hexane solution containing the vinylalane was then concentrated in vacuo and the residue dissolved in 0.5 mL THF (exothermic) in preparation for the cross-coupling reaction.

4.2 Preparation of the Ni(0) Catalyst

In an oven dried 5 mL round bottomed flask containing a stir bar, cooled and purged with argon, was added NiCl$_2$(PPh$_3$)$_2$ (19.6 mg, 0.03 mmol) and the vessel was purged with argon for 2 minutes. THF (0.5 mL) was then added and slow stirring commenced. Slow addition of n-BuLi (0.026 mL, 0.058 mmol) gave a blood-red/black heterogeneous solution which was allowed to stir for 2 min prior to using it in the coupling reaction.

4.3 Coupling of Chloromethylated Tosyate 3 with Vinylalane 2

Chloromethylated tosylate 3 (139.0 mg, 0.375 mmol) was dissolved in THF (0.4 mL) and was cannulated into a solution of vinylalane 2. Two 0.3 mL washings of THF were used to complete the transfer of 3. The Ni(0) catalyst solution (0.188 mL, 0.011 mmol, 3 mol %) was added at room temperature via syringe. The blue-gray solution was then protected from light and allowed to stir at rt for more than about 4 h. The reaction was quenched by the addition of EtOAc (10 mL) and 1 M HCl (20 drops). The mixture was stirred for 10 min to break up the aluminum salts (alternatively, a solution containing 0.3 g citric acid/mL water may be used to quench the reaction, followed by extraction with CHCl$_3$). The layers were separated and the aqueous layer was extracted with EtOAc (3×10 mL). The organics were combined, washed once with brine, dried over anhydrous Na$_2$SO$_4$ and concentrated in vacuo. The resulting pale brown oil was subjected to column chromatography (10% EtOAc/petroleum ether) to give 333.1 mg of a clear, colorless oil (88.6%).

R$_f$=0.28 (10% EtOAc/petroleum ether)

IR (neat) 2963, 2919, 2853, 1741, 1500, 1449, 1372, 1177, 1115, 760 cm$^{-1}$;

$^1$H NMR (400 MHz, CDCl$_3$) δ 7.93 (d, J=4 Hz, 2H), 7.31 (d, J=4 Hz, 2H), 6.62 (s, 1H), 5.07 (m, 9H), 4.98 (t, J=6.4 Hz, 1H), 3.79 (s, 3H), 3.45 (s, 3H), 3.30 (d, J=6.4 Hz, 2H), 2.44 (s, 3H), 2.22 (s, 3H), 2.06 (m, 18H), 1.97 (m, 18H), 1.66 (s, 6H), 1.57 (s, 21H), 1.56 (s, 3H), 1.55 (s, 3H);

$^{13}$C NMR (100 MHz, CDCl$_3$) δ 150.8, 144.5, 142.3, 135.46, 134.99, 134.90, 132.7, 131.2, 128.2, 127.1, 124.4, 124.2, 124.1, 121.8, 113.0, 60.4, 55.9, 39.72, 39.70, 39.65, 26.75, 26.69, 26.4, 25.6, 21.7, 19.7, 17.7, 16.2, 16.0;

LRMS 1026 (M$^+$+Na), 355, 219, 181;

HRFABMS calculated C$_{66}$H$_{98}$NaO$_5$S 1025.7032; found 1025.7077.

Example 5

The tosylate (100.1 mg, 0.10 mmol) was dissolved in Et$_2$O (0.5 mL) and cooled to 0° C. for 5 min. n-BuLi (91 μL, 2.30 M in hexanes, 0.21 mmol) was slowly added and the solution allowed to stir for 3.5 h at 0° C. The reaction was quenched by addition of 1M HCl (5 mL), water (5 mL) and EtOAc (10 mL). The layers were separated and the aqueous phase extracted twice with EtOAc (5 mL). The combined organics were washed with brine, dried over anhydrous Na$_2$SO$_4$, concentrated in vacuo, and chromatographed with 2.5–5.0% EtOAc/petroleum ether to afford 78.7 mg of a clear oil which solidified upon standing overnight to a white solid (92.9%).

TLC, R$_f$=0.48 (10% EtOAc/petroleum ether; mp=49.0–50.5° C.

IR (KBr) 3445, 2964, 2944, 2910, 2845, 1661, 1612, 1584, 1540, 1445, 1341, 1210, 1119, 990, 876, 794, 751, 599, 474 cm$^{-1}$;

$^1$H NMR (400 MHz, CDCl$_3$) δ 6.26 (s, 1H), 5.80 (s, 1H), 5.09 (m, 10H), 3.85 (s, 3H), 3.81 (s, 3H), 3.28 (d, J=6.4 Hz, 2H), 2.21 (s, 3H), 2.04 (m, 18H), 1.97 (m, 18H), 1.75 (s, 3H), 1.66 (s, 3H), 1.58 (s, 24H), 1.55 (s, 3H);

$^{13}$C NMR (100 MHz, CDCl$_3$) δ 149.6, 147.1, 134.8, 133.4, 132.1, 131.1, 124.4, 124.2, 124.1, 122.5, 119.1, 105.3, 60.8, 55.6, 39.7, 39.6, 26.7, 26.6, 26.5, 25.6, 25.1, 19.6, 17.6, 16.1, 16.0;

LREIMS 849 (2.5, M$^+$), 219(11), 181(100), 134(7), 95(13), 81(33), 68(35);

HREIMS calculated for C$_{59}$H$_{92}$O$_3$ 848.7046, found 848.7073.

Example 6

6.1 Synthesis

In a clean 25 mL round bottom flask and stir bar (note: not oven dried and not under argon) the phenol (99.4 mg, 0.117 mmol) was dissolved in toluene (1 mL) and Na$_2$CO$_3$ (36.4 mg, 0.37 mmol) and pyridine (1 μL, 0.012 mmol) were added. Co(salen) (1.9 mg, 0.006 mmol) was then added as a red-purple solid and the reaction vessel was purged with ~0.5 liter O$_2$ and held under an atmosphere of oxygen for the full reaction period. CH$_3$CN (150 μL) was then added to assist in solubilizing the cobalt complex. After 16 h, the reaction mixture was filtered and the supernatant was concentrated in vacuo and then chromatographed (5% EtOAc/petroleum ether) giving 68.6 mg of a red oil which solidified to a orange solid upon standing (69%). The identity of the product was confirmed by $^1$H NMR, mp, HRMS and comparison to authentic sample by HPLC. Purity was established by HPLC at 98%.

TLC: R$_f$=0.22(10%EtOAc/petroleum ether);

mp=44.8–45.9° C.;

$^1$H NMR (400 MHz, CDCl$_3$) δ 5.08 (m, 7H), 4.91 (t, J=7.3 Hz, 1H), 3.96 (s, 3H), 3.95 (s, 3H), 3.15 (d, J=7.2 Hz, 2H), 2.05–1.93 (m, 31H), 171 (s, 3H), 1.65 (s, 3H), 1.57 (s, 21H);

LREIMS 864(15, M$^+$), 235(41), 197(96), 135(12), 121 (12), 107(12), 95(18), 93(18), 80(58), 68(100);

HREIMS calculated for C$_{59}$H$_{90}$O$_4$, 862.6839, found 862.6864.

What is claimed is:

1. A compound of formula:

(I)

wherein,

R$^2$ and R$^3$ are independently selected C$_1$–C$_6$ alkyl groups;

R$^1$ is a C$_1$–C$_6$ unsubstituted alkyl group;

R$^4$ is H or a protecting group which, together with the phenol oxygen to which it is attached is a member selected from silyl ether, ester, carbonate and phosphinate;

R$^5$ is a member selected from the group consisting of an alkyl group which is branched and unsaturated, and —CH$_2$Y, in which Y is OR$^6$, SR$^6$, NR$^6$R$^7$, or halogen;

R$^6$ and R$^7$ are members independently selected from H and branched, unsaturated alkyl.

2. The compound according to claim 1, wherein Y is halogen.

3. The compound according to claim 1, wherein each of R$^1$, R$^2$ and R$^3$ is methyl.

4. The compound according to claim 1, wherein at least one of R$^5$, R$^6$ and R$^7$ has the formula:

wherein, n is a member selected from the integers from 0 to 13.

5. The compound according to claim 4 wherein n is a member selected from the integers from 3 to 9.

6. A compound having a structure of formula:

(VIII)

wherein

R$^2$ and R$^3$ are independently selected C$_1$–C$_6$ alkyl groups;

R$^1$ is a C$_1$–C$_6$ unsubstituted alkyl group; and n is an integer from 0 to 13.

7. A compound of formula:

wherein, $R^2$ and $R^3$ are independently selected $C_1$–$C_6$ alkyl groups;
$R^1$ is a $C_1$–$C_6$ unsubstituted alkyl group;

$R^4$ is substituted or unsubstituted alkyl; and

$R^5$ is a member selected from an alkyl group which is branched and unsaturated and —$CH_2Y$, in which Y is $OR^6$, $SR^6$, $NR^6R^7$, or halogen;

$R^6$ and $R^7$ are members independently selected from H and branched, unsaturated alkyl.

8. The compound according to claim 7, wherein Y is halogen.

9. The compound according to claim 7, wherein each of $R^1$, $R^2$ and $R^3$ is methyl.

10. The compound according to claim 7, wherein at least one of $R^5$, $R^6$ and $R^7$ has the formula:

wherein, n is a member selected from the integers from 0 to 13.

11. The compound according to claim 10 wherein n is a member selected from the integers from 3 to 9.

12. A compound of formula:

wherein, $R^2$ and $R^3$ are independently selected $C_1$–$C_6$ alkyl groups;
R is a $C_1$–$C_6$ unsubstituted alkyl group;

$R^4$ is a protecting group which, together with the phenol oxygen to which it is attached is a member selected from ester, carbonate and phosphinate; and $R^5$ is —C(O)H.

13. The compound according to claim 12, wherein each of $R^1$, $R^2$ and $R^3$ is methyl.

14. A compound having a structure of formula:

wherein $R^2$ and $R^3$ are independently selected $C_1$–$C_6$ alkyl groups;
$R^1$ is a $C_1$–$C_6$ unsubstituted alkyl group;
X+ is a cation; and
n is an integer from 0 to 13.

* * * * *